US008026501B2

(12) United States Patent
Williamson et al.

(10) Patent No.: US 8,026,501 B2
(45) Date of Patent: Sep. 27, 2011

(54) METHOD OF REMOVING OR DEPOSTING MATERIAL ON A SURFACE INCLUDING MATERIAL SELECTED TO DECORATE A PARTICLE ON THE SURFACE FOR IMAGING

(75) Inventors: Mark J. Williamson, Boise, ID (US); Paul M. Johnson, Boise, ID (US); Shawn D. Lyonsmith, Boise, ID (US); Gurtej S. Sandhu, Boise, ID (US); Justin R. Arrington, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 12/869,538

(22) Filed: Aug. 26, 2010

(65) Prior Publication Data

US 2010/0320384 A1 Dec. 23, 2010

Related U.S. Application Data

(62) Division of application No. 11/483,800, filed on Jul. 10, 2006, now Pat. No. 7,791,055.

(51) Int. Cl.
*G01N 21/86* (2006.01)

(52) U.S. Cl. ................................ 250/559.4; 250/208.1

(58) Field of Classification Search ............... 250/559.4, 250/208.1, 221, 559.27; 356/326, 630, 430, 356/237.2–237.5; 438/8, 14, 694
See application file for complete search history.

(56) References Cited

U.S. PATENT DOCUMENTS 4,260,649 A 4/1981 Dension et al.
4,543,486 A 9/1985 Rose
4,579,750 A 4/1986 Bowen et al.
4,581,248 A 4/1986 Roche
4,624,736 A 11/1986 Gee et al.
4,655,849 A 4/1987 Schachameyer et al.

(Continued)

FOREIGN PATENT DOCUMENTS

EP 0756318 A1 1/1997

(Continued)

OTHER PUBLICATIONS

Abramo, M., et al., “Gas Assisted Etching: An Advanced Technique for Focused Ion Beam Device Modification”, Proceedings of the International Symposium for Testing Failure Analysis, (Nov. 13, 1994), 439-446 pgs.

(Continued)

*Primary Examiner* — Que T Le
(74) *Attorney, Agent, or Firm* — Schwegman, Lundberg & Woessner, P.A.

(57) ABSTRACT

A method that may be applied to imaging and identifying defects and contamination on the surface of an integrated circuit is described. An energetic beam, such as an electron beam, may be directed at a selected IC location having a layer of a solid, fluid, or gaseous reactive material formed over the surface. The energetic beam disassociates the reactive material in the region into chemical radicals that either chemically etch the surface preferentially, or deposit a thin layer of a conductive material over the local area around the energetic beam. The surface may be examined as various layers are selectively etched to decorate defects and/or as various layers are locally deposited in the area around the energetic beam. SEM imaging and other analytic methods may be used to identify the problem more easily.

30 Claims, 5 Drawing Sheets

IMAGER
ENDPOINT DETECTOR
BEAM
232
236
234
INLET
238
240
220
H*
214
DIELECTRIC
216
DIELECTRIC
210
S/D
204

U.S. PATENT DOCUMENTS 4,668,304 A 5/1987 Schachameyer et al.
4,670,063 A 6/1987 Schachameyer et al.
4,670,064 A 6/1987 Schachameyer et al.
4,685,976 A 8/1987 Schachameyer et al.
4,694,777 A 9/1987 Roche
4,735,822 A * 4/1988 Ohtoshi et al. ................ 427/582
4,832,781 A 5/1989 Mears
4,933,206 A 6/1990 Cox
4,938,996 A 7/1990 Ziv et al.
4,940,505 A 7/1990 Schachameyer et al.
4,980,198 A 12/1990 Dowben et al.
5,032,435 A 7/1991 Biefeld et al.
5,047,649 A 9/1991 Hodgson et al.
5,102,830 A 4/1992 Sandhu
5,140,164 A 8/1992 Talbot et al.
5,155,053 A 10/1992 Atkinson
5,164,222 A 11/1992 Gottsleben et al.
5,326,981 A 7/1994 Hara et al.
5,387,443 A 2/1995 Ota et al.
5,403,433 A 4/1995 Morrison et al.
5,429,730 A 7/1995 Nakamura et al.
5,438,019 A 8/1995 Sandhu
5,472,935 A 12/1995 Yandrofski et al.
5,508,368 A 4/1996 Knapp et al.
5,622,567 A 4/1997 Kojima et al.
5,639,342 A 6/1997 Chen et al.
5,641,545 A 6/1997 Sandhu
5,648,114 A 7/1997 Paz De Araujo et al.
5,682,041 A 10/1997 Kawakubo et al.
5,733,609 A 3/1998 Wang
5,754,297 A 5/1998 Nulman
5,759,923 A 6/1998 McMillan et al.
5,800,617 A 9/1998 Sandhu
5,807,650 A 9/1998 Komano et al.
5,825,035 A 10/1998 Mizumura et al.
5,834,331 A 11/1998 Razeghi
5,942,854 A 8/1999 Ryoji et al.
5,976,328 A 11/1999 Azuma et al.
5,985,693 A 11/1999 Leedy
5,989,928 A 11/1999 Nakata et al.
6,051,287 A 4/2000 Marsh
6,064,800 A 5/2000 Sandhu
6,091,071 A 7/2000 Franz et al.
6,113,751 A 9/2000 Morgenthaler
6,143,085 A 11/2000 Marsh
6,177,147 B1 1/2001 Samukawa et al.
6,187,492 B1 2/2001 Ri et al.
6,194,325 B1 2/2001 Yang et al.
6,214,183 B1 4/2001 Maishev et al.
6,281,072 B1 8/2001 Li et al.
6,291,341 B1 9/2001 Sharan et al.
6,309,972 B1 10/2001 Pio
6,310,341 B1 10/2001 Todokoro et al.
6,462,333 B1 10/2002 Gersonde
6,499,425 B1 12/2002 Sandhu et al.
6,573,199 B2 6/2003 Sandhu et al.
6,613,702 B2 9/2003 Sandhu et al.
6,661,005 B1 12/2003 Bruenger
6,683,005 B2 1/2004 Sandhu et al.
6,720,272 B2 4/2004 Sandhu et al.
6,730,367 B2 5/2004 Sandhu
6,753,538 B2 6/2004 Musil et al.
6,764,856 B2 7/2004 Holmes et al.
6,787,783 B2 9/2004 Marchman et al.
6,793,736 B2 9/2004 Sandhu et al.
6,797,337 B2 9/2004 Dando et al.
6,809,317 B2 10/2004 Vandervorst
6,811,615 B2 11/2004 Sun
6,838,114 B2 1/2005 Carpenter et al.
6,838,121 B2 1/2005 Weimer
6,845,734 B2 1/2005 Carpenter et al.
6,869,479 B2 3/2005 Shafeev et al.
6,897,907 B2 5/2005 Morimitsu
6,911,832 B2 6/2005 Kolachina et al.
7,113,276 B1 9/2006 Higgs et al.
7,122,125 B2 10/2006 Deshmukh et al.
7,238,294 B2 7/2007 Koops et al.
7,256,405 B2 8/2007 Nakasuji et al.
7,262,555 B2 8/2007 Rueger et al.
7,303,690 B2 12/2007 Amemiya et al.
7,311,947 B2 12/2007 Dando et al.
7,452,477 B2 11/2008 Koops et al.
7,569,484 B2 8/2009 Rueger et al.
7,718,080 B2 5/2010 Rueger et al.
7,791,055 B2 9/2010 Williamson et al.
7,791,071 B2 9/2010 Rueger et al.
7,807,062 B2 10/2010 Williamson et al.
7,833,427 B2 11/2010 Rueger et al.
7,892,978 B2 2/2011 Williamson et al.
2002/0173124 A1 11/2002 Joo
2002/0182542 A1 12/2002 Choi et al.
2003/0047691 A1 3/2003 Musil et al.
2003/0170389 A1 9/2003 Sandhu
2003/0201391 A1 10/2003 Shinada et al.
2004/0036398 A1 2/2004 Jin
2004/0048398 A1 3/2004 Liang et al.
2004/0091638 A1 5/2004 Haight et al.
2004/0097076 A1 5/2004 Iyer et al.
2004/0113097 A1 6/2004 Marchman et al.
2004/0124348 A1 7/2004 Utz et al.
2004/0140437 A1 7/2004 Bukofsky et al.
2004/0151991 A1 8/2004 Stewart et al.
2005/0078462 A1 4/2005 Dando et al.
2005/0087514 A1 4/2005 Koops et al.
2005/0212092 A1 9/2005 Nishizawa
2005/0253093 A1 11/2005 Gorski et al.
2005/0266168 A1 12/2005 Poullos
2006/0134920 A1 6/2006 Liang
2006/0147814 A1 7/2006 Liang
2006/0154477 A1 7/2006 Geng et al.
2006/0183055 A1 8/2006 O'Neill et al.
2006/0201911 A1 9/2006 Edelberg et al.
2006/0228634 A1 10/2006 Bret et al.
2006/0288937 A1 12/2006 Dando et al.
2006/0289969 A1 12/2006 Dando et al.
2007/0158303 A1 7/2007 Nasser-Ghodsi et al.
2007/0158304 A1 7/2007 Nasser-Ghodsi et al.
2007/0228002 A1 10/2007 Geng et al.
2007/0228296 A1 10/2007 Mouttet
2007/0257212 A1 11/2007 Mouttet
2007/0278180 A1 12/2007 Williamson et al.
2008/0006603 A1 1/2008 Williamson et al.
2008/0006786 A1 1/2008 Williamson et al.
2008/0009140 A1 1/2008 Williamson et al.
2008/0038863 A1 2/2008 Rueger et al.
2008/0038894 A1 2/2008 Rueger et al.
2008/0038928 A1 2/2008 Rueger et al.
2008/0038933 A1 2/2008 Rueger et al.
2009/0288603 A1 11/2009 Rueger et al.
2010/0221922 A1 9/2010 Rueger et al.
2010/0314354 A1 12/2010 Rueger et al.
2011/0017401 A1 1/2011 Williamson et al.
2011/0056625 A1 3/2011 Rueger et al.

FOREIGN PATENT DOCUMENTS

EP 1363164 A1 11/2003
JP 09064030 A2 3/1997
JP 2004-257845 9/2004
WO WO-2008008156 A2 1/2008
WO WO-2008008156 A3 1/2008
WO WO-2008008157 A2 1/2008
WO WO-2008008157 A3 1/2008
WO WO-2008008159 A2 1/2008
WO WO-2008008159 A3 1/2008
WO WO-2008021363 A2 2/2008
WO WO-2008021363 A3 2/2008

OTHER PUBLICATIONS

Abramo, M. T, et al., "The application of advanced techniques for complex focused-ion-beam device modification", Reliability of electron devices, failure physics and analysis, 1996. Proceedings of the 7th europeon symposium on Oct. 8-11, 1996, Piscataway, NJ, USA, IEEE, 1775-1778 pgs.

Alers, G., et al., "Interlevel Dielectric Failure in Copper/Low-K Structures", IEEE, Transactions on Devices and Material Reliability 36, (2004), 148-152.

Fujii, Toshiaki, et al., "A nanofactory by focused ion beam", Journal of Micromechanics and Microengineering, 15(10), (2005), S286-S291.
Fujioka, H., et al., "Measurements of the Energy Dependence of Electron Beam Assisted Etching of, and Deposition on, Silica", Journal of Physics D. Applied Physics, IOP Publishing, Bristol, GB, vol. 23, No. 2, (Feb. 14, 1990), 266-268 pgs.
Golub, M., "Scanning electron microscope investigations of highly conducting organic composites", Journal of Material Sciences 36, (2001), 5543-5550.
Jonge, N., et al., "High brightness electron beam from a multi-walled carbon nanotube", Nature vol. 420, (Nov. 28, 2002), 393-395.
Liao, J. Y, et al., "Etch characterization of packaged IC samples in an RIE with endpoint detection by ICP source for failure analysis applications", Physical and failure analysis of integrated circuits, 2005, IPFA 2005. Proceedings of the 12th International Symposium on the Shangri-LA's RASA Sentosa Resort, Singapore Jun. 27-Jul. 1, 2005 Piscataway, NJ, USA, IEEE, 123-126 pgs.
Marcoux, P. J, et al., "Methods of end point detection for plasma etching", Solid State Technology, Pennwell Corporation, Tulsa, OK, US, vol. 25, (Apr. 1981), 115-122 pgs.
Numajiri, T., et al., "Sample Preparation for electron beam testing with reactive ion etching", Physical and Failure Analysis of Integrated circuits,1997, Proceedings of the 1997 6th International Symposium on Singapore Jul. 21-25, 1997, New york, USA, 56-61 pgs.
Randolph, S., et al., "Focused electron-beam-induced etching of silicon dioxide", Journal of Applied Physics, American Institute of Physics, 98, (Aug. 3, 2005), 34902-34902.
Sanchez, E. J, et al., "Ion and electron beam assisted growth of nanometric sl m on structures for near-field microscopy", Review of scientific instruments, AIP, Melville, NY, US, vol. 73, No. 11, (Nov. 2002), 3901-3907 pgs.
Teo, K., et al., "Fabrication and Electrical Characteristics of carbon nanotube-based microcathodes for use in a parallel elecron-beam lithography system", Journal of Vacuum Science & Technology B: Microelectronics Processing and Phenomena, vol. 21, (Mar. 2003), 693-697.
Wang, J, et al., "Etching characteristics of chromium thin films by an electron beam induced surface reaction", Semicond. Sci. Technol., 18, (2003), 199-205.
Wood, L., "Plasma Cleaning of Chip Scale Packages for Improvement of Wire Bond Strength", IEEE, International Symposium on Electronic Materials and Packaging, (2000), 406-408.

* cited by examiner

METHOD OF REMOVING OR DEPOSTING MATERIAL ON A SURFACE INCLUDING MATERIAL SELECTED TO DECORATE A PARTICLE ON THE SURFACE FOR IMAGING

RELATED APPLICATION

This application is a Divisional of U.S. application Ser. No. 11/483,800, filed Jul. 10, 2006, now U.S. Pat. No. 7,791,055, which is incorporated herein by reference in its entirety.

TECHNICAL FIELD

This application relates generally to semiconductor devices and device testing and, more particularly, to detection and analysis of defects and errors associated with electrical function failures and long term reliability failures in integrated circuit (IC) devices, including individual die, packaged die or die still on semiconductor wafers, such as memory devices, logic devices and microprocessors.

BACKGROUND

The semiconductor device industry has a market driven need to reduce IC device failures at electrical test, and to improve the operational lifetimes of IC devices. Reduced device failures may result in increased IC fabrication yield and improved device operational lifetime. Increased IC fabrication yields may result in decreased IC prices, and improved market share.

One method to reduce the number of device failures is to analyze failed devices and determine the cause of the failure. The failures may be what are known as field failures that occur at customer sites, or they may occur in products that have been sold to consumers. The failures may be found during wafer level testing at the end of wafer fabrication, or in testing after a supposedly good IC die is placed in a package, or in testing after a supposedly good IC package is placed in a printed circuit board (PCB).

It is known to examine failed devices by means of electrical testing, optical microscopes, transmitting electron microscopes (TEM), scanning electron microscopes (SEM), and other well known methods. If, for example, a particle is found that produces a short between two conductive lines in a signal layer, then action may be taken at the fabrication site to reduce particle levels, and thus increase fabrication yield. This method may be used in cases where the failure, such as the illustrative particle just discussed, is at, or near, the surface of the sample, since the failure may not be otherwise visible in an optical or an electron microscope.

However, as the semiconductor device industry has increased the level of integration of their devices and packed more capability on ever smaller semiconductor chips, the critical dimension, or size, of each transistor, each conductive line, and the spacing between lines has decreased. As a result of the smaller lines and smaller spaces, the size of a defect that may result in a device failure has also decreased, which means that the same defects and particles that were not likely to cause failures in previous generations of electronic devices are now device killers. The smaller defects are harder to detect and observe with the existing methods of detection and evaluation, and some method to enlarge the defects, which may be known as decorating, or of increasing the defect contrast as compared with the device background is needed to improve defect detection.

A method is needed to chemically etch a small area around a defect with high selectivity between the etch rates of the materials forming the defect and the materials forming the semiconductor substrate. This would improve the visual and SEM delineation, or contrast, between the defect and the substrate. In addition, or in the alternative, a layer of conductive material needs to be deposited, either selectively or non-selectively, on the surface of the substrate to decorate the defect, thus improving the ability to observe the defect. The ability to observe the defect during the localized etching and/or deposition, and the ability to stop the etching or decorating when the best image is obtained would also be beneficial. The ability to analyze the composition of the materials being etched or decorated prior to beginning the enhancement process, would improve the proper selection of the optimum etch mixture and conditions. With such an arrangement, the defect sample may be imaged during the small spot localized etching and/or deposition, and the process may continue until the desired level of decoration or enhancement structure is obtained.

These and other aspects, embodiments, advantages, and features will become apparent from the following description and the referenced drawings.

DETAILED DESCRIPTION

Figure 1:
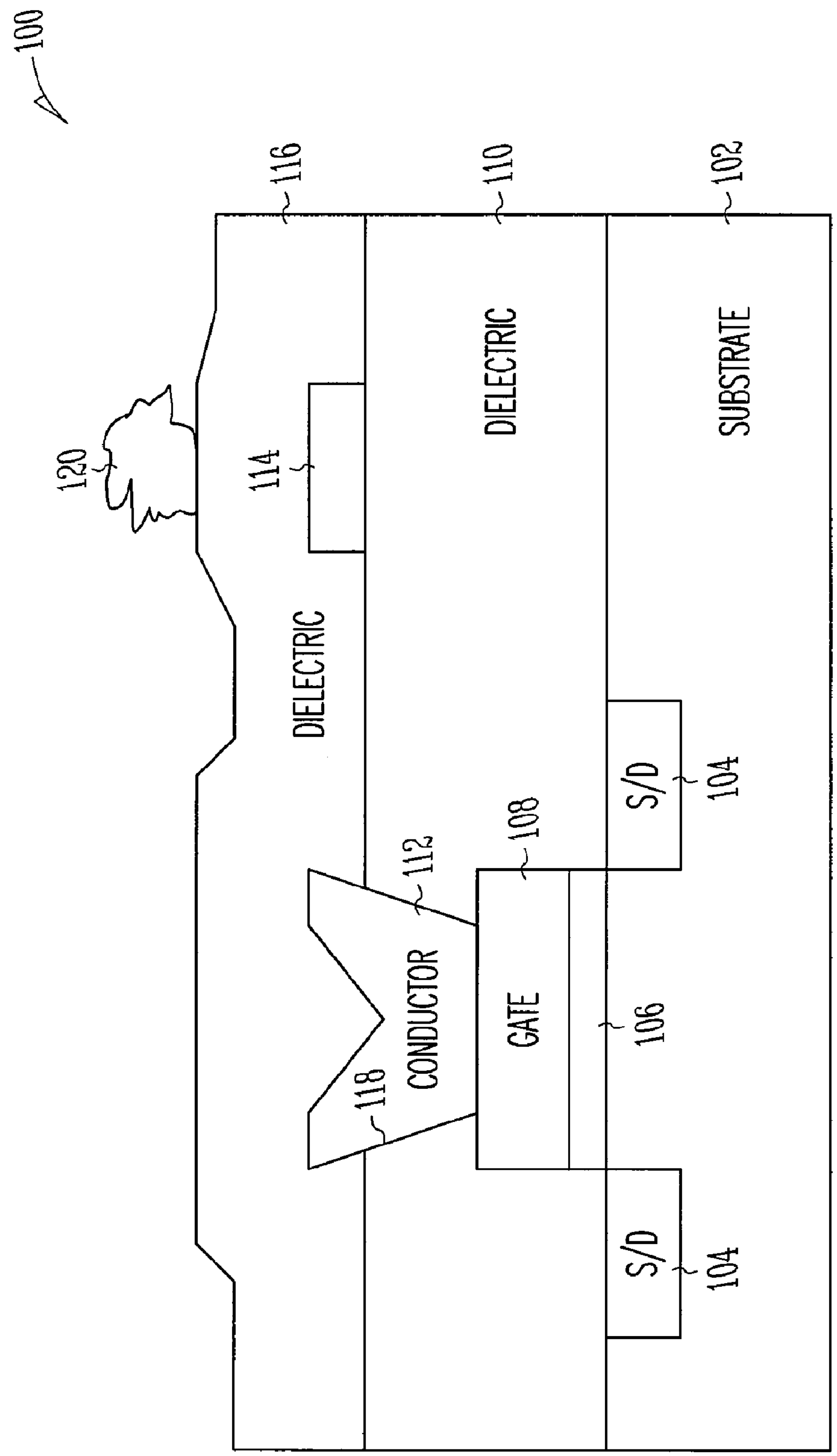
FIG. 1 illustrates a semiconductor device in cross section.

The following detailed description refers to the accompanying drawings that show, by way of illustration, specific aspects and embodiments in which the present invention may be practiced. These embodiments are described in sufficient detail to enable those skilled in the art to practice the present invention. Other embodiments may be utilized and structural, logical, and electrical changes may be made without departing from the scope of the present invention. The various embodiments are not necessarily mutually exclusive, as some embodiments can be combined with one or more other embodiments to form new embodiments.

The term "horizontal" as used in this application is defined as a plane parallel to the conventional plane or surface of a wafer or substrate, regardless of the orientation of the wafer or substrate. The term "vertical" refers to a direction perpendicular to the horizontal as defined above. Prepositions, such as "on", "side" (as in "sidewall"), "higher", "lower", "over" and "under" are defined with respect to the conventional plane or surface being on the top surface of the wafer or substrate, regardless of the orientation of the wafer or substrate. The following detailed description is, therefore, not to be taken in a limiting sense, and the scope of the present disclosure is defined only by the appended claims, along with the full scope of equivalents to which such claims are entitled.

The described embodiments provide a method for localized accelerated selective chemical etching of an integrated circuit (IC) to improve contrast between different materials on the IC surface, or to deposit materials locally on the surface of the IC to enlarge or decorate defects. The detection of surface defects having ever decreasing dimension may require exaggeration of the structure of the defect. Electron induced chemical etching and deposition can be used to increase the contrast of defects, and to decorate the defects, resulting in increased visibility of surface defects in SEM and optical micrographs. Depositing a material with more favorable imaging properties than the defect or substrate improves imaging efficiency, and may increase the size of the defect. As an illustrative example, it is difficult to detect small nitride flakes produced when a nitride surface is scratched, as may typically occur either by handling, vibration or transportation. The visibility of the nitride flake may be enhanced by depositing a thin layer of chromium on the surface of the IC, either a chip or a wafer. The layer of chromium may be thinner than 2 nm, and may help dissipate charge build up in a SEM image. The chromium has a higher electron yield as compared to nitride, and increases the signal to noise ratio in a SEM image. The addition of the chromium layer to the particle increases the particle size, while the addition of the chromium to the substrate has little proportional effect on the appearance of the substrate, thus improving the visibility of the particle in SEM and in optical microscopes. The chromium is reflective and bright under optical microscopes, particularly in what is known as black field illumination mode, and thus improves the visibility of the particle.

Etching may also be used to enhance imaging efficiency by exaggerating the contours of the defect to increase contrast and visibility, especially along edges and material boundaries. In the illustrative example of a particle formed of a different material than the substrate, the use of an etch composition having a preferential etch rate for the substrate material exaggerates the surface in the vicinity of the particle, due to the masking effect of the particle. The particle may be more visible due to the increased area and topographical height differences caused by the etching of the substrate material in the region near the defect. This method may be particularly useful in enhancing the image of particles formed by environmental contamination such as dust, or for metallic particles from handling the IC with processing tools.

In an embodiment, the localized chemical accelerator is an energetic beam, such as an electron beam, and the excited material is a halogen containing compound, forming a layer on, or immediately above, the surface of the IC in a vacuum chamber, such as inside a scanning electron microscope (SEM). Localized electron beam assisted chemical etching provides a method of localized selective etching or decoration deposition, as may be useful in IC failure analysis of defects.

In an illustrative embodiment, localized etching to increase contrast may occur by passing a halogen containing gaseous material over the surface of the IC chip in the vacuum chamber, and exciting the halogen atoms with an electron beam to form chemical radicals. By controlling the vacuum pressure and the gas flow, the mean free diffusion length (and equivalently the lifetime) of the radicals may be controlled, and the etching of the IC surface may be substantially confined to a desired region around the electron beam. Electrons from the primary beam, electrons scattered from the IC surface, as well as secondary electrons and ionizing radiation emitted from the IC surface may all cause the formation of the radicals by dissociating the individual molecules or atoms of the halogen containing layer. The halogen containing layer may be adsorbed onto the surface of the IC, as may occur when using a source material such as xenon difluoride, which sublimates in a vacuum and may deposit on the surface of the IC.

FIG. 1 illustrates a semiconductor device 100, having a substrate 102, with a series of conductive regions 104 formed in or on the substrate. The conductive regions 104 may be formed from diffused portions of the substrate 102, from doped polysilicon, or from various metals and metal silicides. Above the conductors 104 is a dielectric layer 106, and a gate electrode 108. The gate electrode 108, the gate dielectric 106, and the conductive regions 104, form a typical semiconductor device, with a protective dielectric layer 110, and signal and power interconnections 112 and 114. The various conductive materials 112 and 114 may be pure materials or combinations of materials, such as copper doped aluminum, or may be formed of multiple layers, such as having titanium, or titanium-tungsten, or titanium nitride barrier layers under the conductors 112 or 114. The conductors 112 and 114 are protected from environmental problems such as scratches and ionic contamination by a dielectric layer 116, and selected conductors may electrically connect to the gate electrode 108 by a contact hole 118 in the dielectric layer 110.

The dielectric layer 116 is shown in the illustrated embodiment with a particle 120 on the surface. Examples of such particles may include a chipped piece of the dielectric 116 caused by a handling error such as a scratch, or may be a particle of the same composition as the dielectric 116 that fell upon the device at the end of the deposition process that formed dielectric layer 116. Other examples include metal particles from the machinery that handles and transports the semiconductor wafers in processing, and environmental contaminants. In the case where the particle 120 is of the same basic composition as the dielectric layer 116, detecting and imaging the particle may be difficult, since the particle properties are similar to the background material. The present method provides a method of either removing a small amount of the dielectric layer 116, so that the contrast between the particle 120 and the dielectric 116 may be improved.

Figure 2:
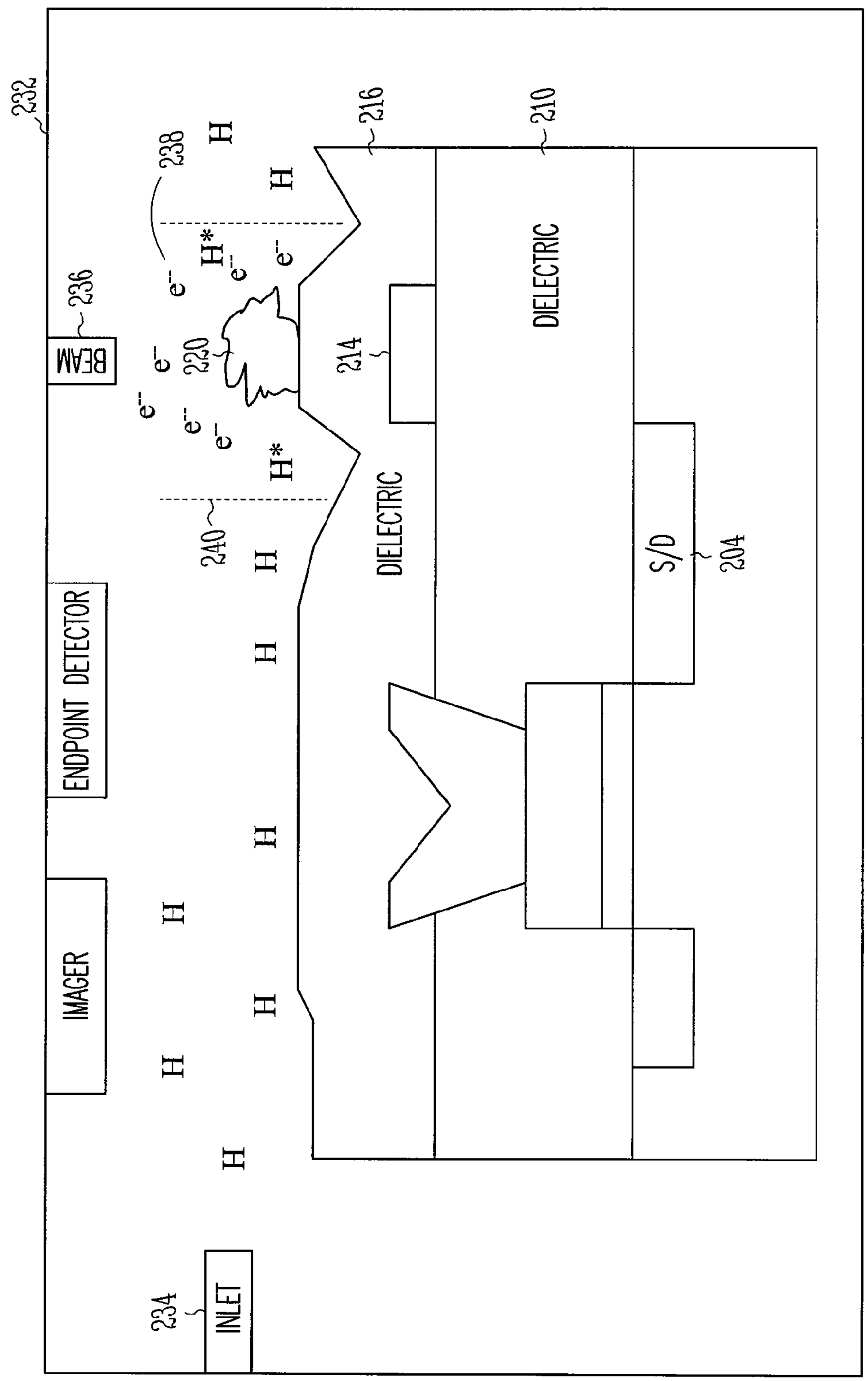
FIG. 2 illustrates the semiconductor device of FIG. 1 in a vacuum chamber in accordance with an illustrative embodiment.

FIG. 2 illustrates the semiconductor device of FIG. 1 in a vacuum chamber 232, in an embodiment, a SEM, having a vacuum pump (not shown for simplicity), an inlet 234, and an energetic beam 236, such as an electron beam, which may be movable. The inlet 234 may be a directed gas jet as shown, or a sublimation port, a gas shower head, a bubbler, or a liquid material sprayer, such as an atomizer. The inlet 234 supplies the region around the top surface of the sample with a material that is either reactive, or may be made reactive, such as a halogen containing material. The atoms of the halogen in this illustrative example are shown as floating "H" symbols, some of which are adsorbed onto the surface of the sample, and some diffusing around the chamber 232.

The vacuum chamber 232 has a directed and focused energetic beam device 236, which in an embodiment is a SEM beam, directed to a desired location on the surface of the sample. The electron beam device 236 emits electrons 238 (shown as "$e^-$" symbols) which excite the halogen molecules or atoms (H) floating in the vacuum chamber 232, or adsorbed onto the surface of the sample, and form a chemically reactive radical, denoted by "H*". Due to the limited lifetime of the radicals, the radicals H* are limited to the area around the electron beam 236 shown by the dotted lines 240. The selected radicals H* have a much greater chemical etch rate on the dielectric layer 216, than the halogen molecules or atoms (H), and thus the etching of the two shown pits on either side of the particle 120 (which represents the generally circular or annular etch region in three dimensions) occurs wherever the illustrative electron beam forms the H* radicals. In an illustrative embodiment, the halogen compound is xenon difluoride, which forms fluorine radicals when excited by the electron beam. The fluorine radicals have a large etch rate on the top dielectric layer 216, but the areas immediately under portions of the particle 220 are not etched as rapidly due to shadowing. In such a fashion, it is possible to etch pits in the dielectric 216 to improve the visual and SEM contrast around the particle 120.

Figure 3:
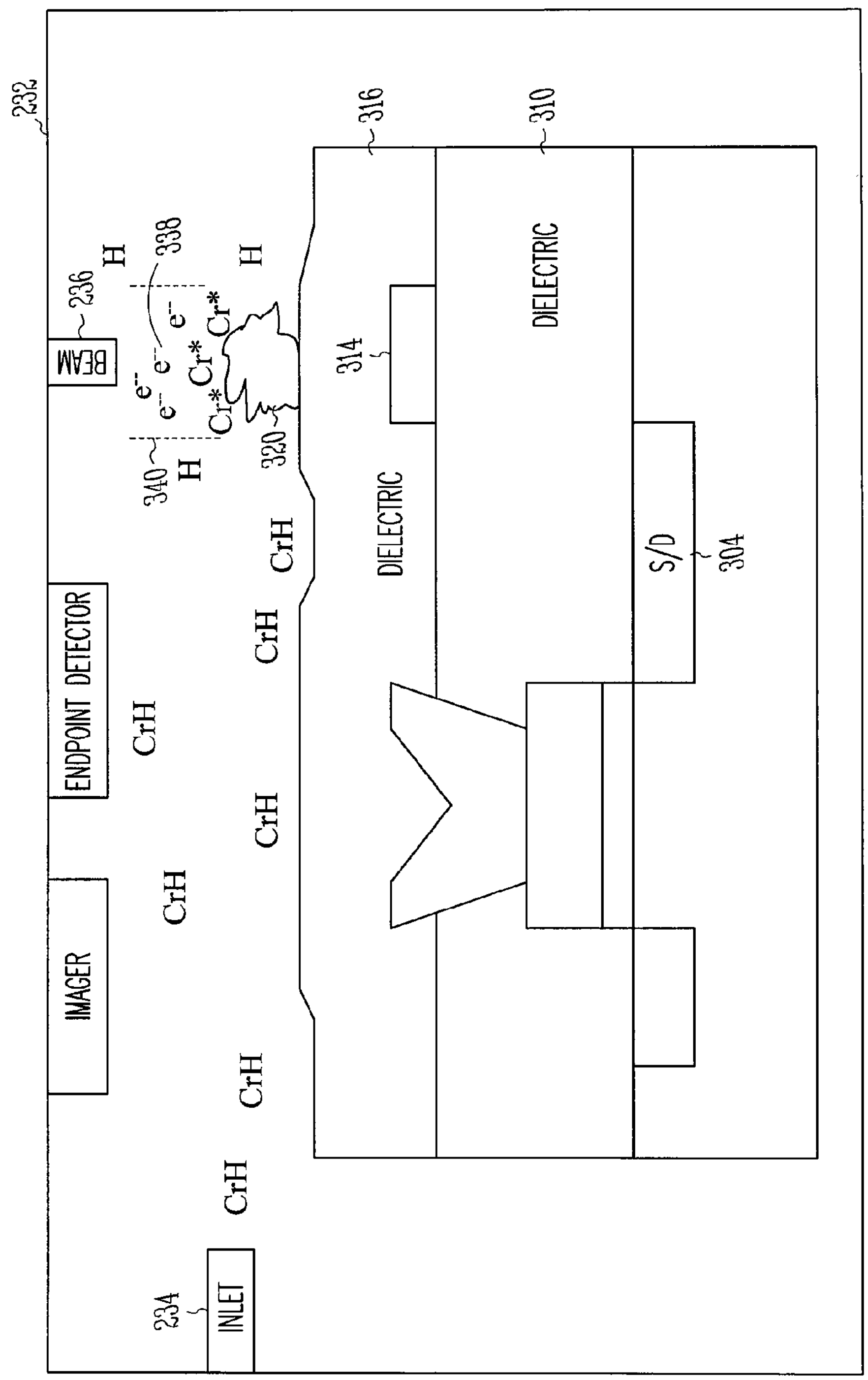
FIG. 3 illustrates the semiconductor device of FIG. 1 in another illustrative embodiment.

FIG. 3 illustrates another illustrative embodiment of the device of FIG. 1, after a period of local deposition of an illustrative decorative layer on the particle 320. In this illustrative embodiment, the potential solution to the problem of imaging and detecting the particle 320 is to decorate the particle by increasing its relative size and electron yield by coating the particle with a conductive material such as chromium. In this embodiment the injector 334 introduces a chromium halide material, indicated as CrH. The illustrative energetic beam apparatus 336 (in this embodiment an electron beam) having sufficient energy to create chemical radicals denoted by Cr*, in a chromium halide material CrH, which is a gas in this embodiment that is either floating in the vacuum in vacuum chamber 332, or adsorbed onto the surface of the IC or onto the surface of the particle 320. The energetic beam causes the formation of a chromium metal layer on the particle 320. In an embodiment, the chromium layer is from 1-100 nanometers in thickness, and decorates the particle for easier detection and evaluation. In an embodiment, the thickness of the chromium metal is determined by SEM observation during the metal deposition, and direct determination of the best image quality. In other embodiments, depending upon the vapor pressure of the chromium containing material under the specific vacuum conditions, the chromium may be in the form of liquid droplets, or a solid formed on the surfaces of the particle and the substrate within the limits of the beam edges 240. In such a fashion, it is possible to cause chromium halide to disassociate and deposit chromium metal to improve the imaging and detection of the particle 320.

In an embodiment, the etching shown in FIG. 2 is combined with the deposition discussed with regard to FIG. 3, to further maximize the defect delectability. In another embodiment, the etching and depositing may be used to remove a layer from the IC and decorate and image a defect in a buried layer. In yet another embodiment, the chemical radicals include a silicon containing material such as silane or TEOS and an oxygen containing material and a hole etched in the IC may be filled to repair the IC and return it to operational condition.

Figure 4:
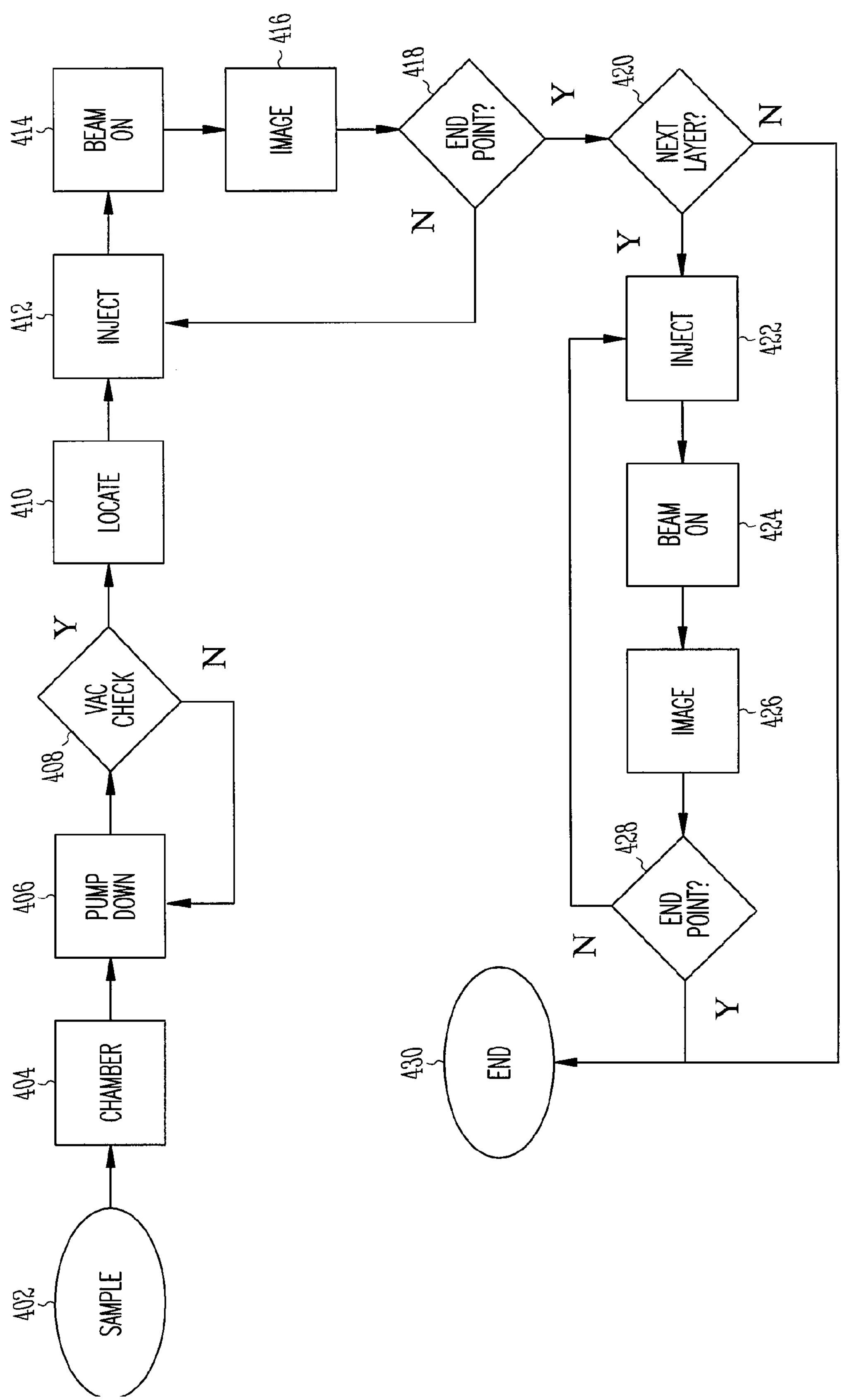
FIG. 4 is a flowchart of the method in accordance with an illustrative embodiment.

FIG. 4 is a flow diagram showing the method for electron induced chemical etching for device level diagnosis of potential problems. The method starts at 402 with obtaining a sample, such as an IC, for decoration or contrast etch. At 404 the sample is placed in a vacuum chamber, such as a SEM, and the chamber begins to be evacuated at 406. At 408, it is decided whether or not the chamber has been pumped to a desired vacuum pressure, which may be used to control the mean free path of the radicals generated by the electron beam. If the desired pressure is not yet obtained, the method returns to 406. When the proper vacuum level is reached the method uses a beam locator device, such as a SEM, to find the desired location at 410. At 412 the reactive material is injected into the vacuum chamber at a controlled rate, which in conjunction with the control of the vacuum pressure and the beam energy and intensity, may determine the production rate of the chemical radicals. The electron beam is turned on at a desired energy and beam intensity at 414, which depending upon the selected reactive material composition and pressure begins the chemical etching or material deposition, such as chrome, of at least some portion of the sample surface towards which the electron beam is directed. The reaction products are removed by the vacuum system.

At 416, the surface is examined by imaging the etch region with a SEM, and it is determined if the desired level of decoration and/or contrast of the IC and defect has been reached. An endpoint to the etching may be directly observable by SEM by the acquisition of an image of the defect, or the reaction products from any etching that may be done may be analyzed by any of a variety of down stream analytic methods, such as RGA, to determine if the material being etched has a specific composition, such as may occur when a buried layer is reached. Other endpoints may include the time of the etching and decoration deposition, a thickness of the top layer removed by etching, or a thickness of the deposited layer of decoration, such as a metal thickness. The exposed surface and the imaged particle or other defect may also be analyzed by SEM based analysis methods, such as EDAX or XES to determine the properties of the particle. At 418, it is determined whether the current processing of the IC top layer material has been etched or deposit decorated sufficiently to provide optimum defect imaging. If not, the method returns to 412.

If the current layer contrast etching and decoration deposition has been completed, then it is determined at 420 if there is an additional layer that needs to be etched, for example, to enable removal of a particle, or whether there is to be a localized etch or deposition done to fix the defect, as may occur if a metal particle has shorted out two signal or power lines. If not, the method ends at 430.

If there is another process to complete prior to ending the method, then a new reactive material may be injected into the vacuum chamber at 422, the electron beam is turned on to the desired energy level and intensity at 424, and the etch or deposition process result is imaged and analyzed at 426 as previously done at 416. At 428, it is determined if the present process has completed the etching or deposition. If not the method returns to 422. If the additional process is completed and images are formed, then the method ends at 430. In this fashion, the IC defect imaged in the first portion of the exemplary process, may be repaired and returned to service or testing.

Figure 5:
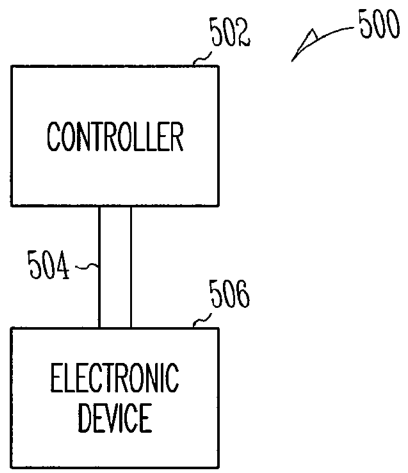
FIG. 5 is a block diagram of an electronic device in accordance with an embodiment of the invention.

FIG. 5 is a block diagram of a general electronic device in accordance with an embodiment of the invention with an electronic system 500 having one or more device defects image enhanced and/or repaired according to various embodiments of the present invention. Electronic system 500 includes a controller 502, a bus 504, and an electronic device 506, where bus 504 provides electrical conductivity between controller 502 and electronic device 506. In various embodiments, controller 502 and/or electronic device 506 include an embodiment for a portion of the device having an IC die defects image enhanced and/or repaired as previously discussed herein. Electronic system 500 may include, but is not limited to, information handling devices, wireless systems, telecommunication systems, fiber optic systems, electro-optic systems, and computers.

Figure 6:
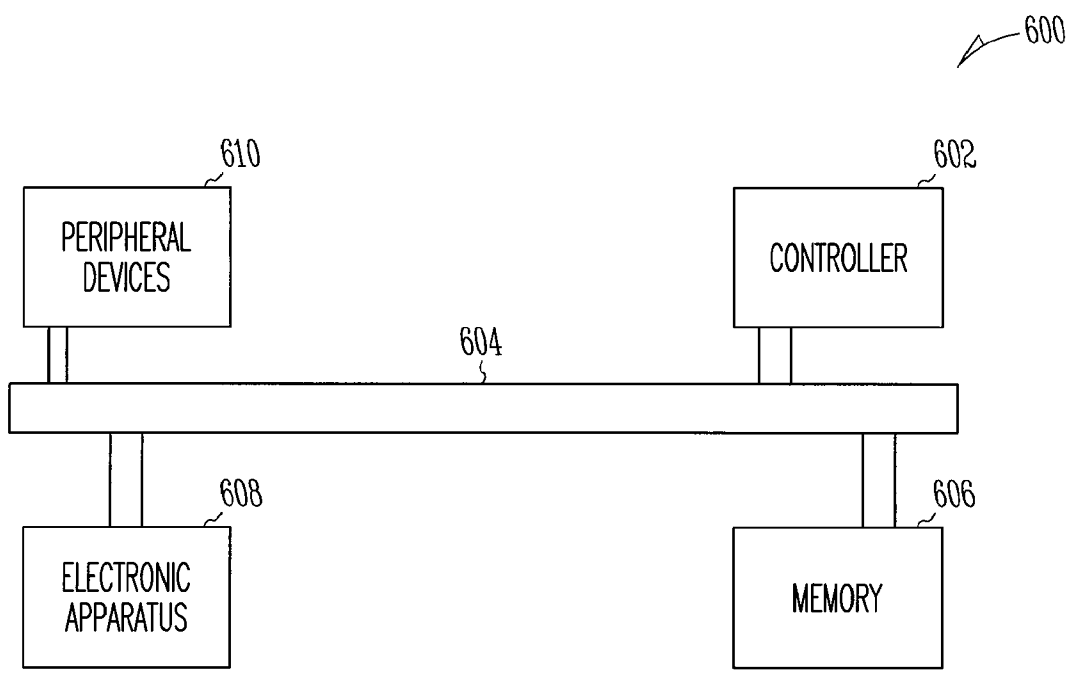
FIG. 6 is a diagram of an electronic system having devices in accordance with an embodiment of the invention.

FIG. 6 depicts a diagram of an embodiment of a system 600 having a controller 602 and a memory 606. Controller 602 and/or memory 606 include a portion of the circuit having IC devices and memory chips with defects image enhanced and/or repaired in accordance with the disclosed embodiments. System 600 also includes an electronic apparatus 608, and a bus 604, where bus 604 may provide electrical conductivity and data transmission between controller 602 and electronic apparatus 608, and between controller 602 and memory 606. Bus 604 may include an address, a data bus, and a control bus, each independently configured. Bus 604 also uses common conductive lines for providing address, data, and/or control, the use of which may be regulated by controller 602. In an embodiment, electronic apparatus 608 includes additional memory devices configured similarly to memory 606. An embodiment includes an additional peripheral device or devices 610 coupled to bus 604. In an embodiment, controller 602 is a processor. Any of controller 602, memory 606, bus 604, electronic apparatus 608, and peripheral device or devices 610 may include ICs treated in accordance with the disclosed embodiments. System 600 may include, but is not limited to, information handling devices, telecommunication systems, and computers. Peripheral devices 610 may include displays, additional memory, or other control devices operating with controller 602 and/or memory 606.

CONCLUSION

A method is presented for enhancing detection of defects on or under an IC device surface by positioning the sample in a vacuum chamber, and creating a layer of a reactive material in proximity with the surface of the IC. The layer of reactive material may be excited by an energetic beam to form chemical radicals in the region surrounding the energetic beam. The radicals may remove a portion of the surface of the structure by chemical etching until the desired amount of etching needed to improve the contrast ratio between the defect and the sample substrate is obtained. The material removed from the surface may also be analyzed to characterize the material in various ways. With such an arrangement, the defects on an IC chip may be enhanced and made more detectable. The method may also be used to form localized depositions of dielectric or conductive materials as needed to improve the size or conductivity of the defects, which may improve the ability of a scanning electron microscope to image and detect the defects.

The reactive material may comprise various types of halogen in gaseous, liquid or solid form to form an etching ambient that may be either selective for one material over another, or may be non-selective. The reactive material may comprise various metallo-organic or metallo-halide materials to form a deposition ambient, which may also be either selective for deposition on one material and not on another, or may be non-selective and form a deposition relatively evenly over the selected small spot surrounding the energetic beam. In an embodiment, the reactive material is xenon fluoride, which is a solid at standard temperature and pressure, and sublimes in the vacuum chamber. In an embodiment, the reactive material includes chromium, which has a greater conductivity than dielectric materials and thus helps dissipate charge buildup in a SEM image. Chromium has a higher electron yield than dielectric layers, which increases the signal to noise ratio in a SEM image. Chromium also decorates various defects, such as particles, by increasing the size of the defect, making detection of small defects easier.

The reactive material may be directed to the region near the surface of the IC chip by a formed jet of vapor or may simply be allowed to diffuse through the vacuum chamber. The reactive material may be adsorbed onto the surface of the material, or may be a gas in the vicinity of the surface, or may condense or precipitate onto the surface. The reactive material may be a mixture of materials (that is chemical precursors) which react with one another, especially when activated or excited to form chemical radicals by the energetic beam, and may include a material that does not directly interact with the other reactive materials, but rather acts as a reaction catalyst, an inhibitor, promoter, or reaction buffer.

The method of exciting the layer of reactive materials may use an energetic beam such as an electron beam. The electron beam may have a diameter of less than 0.01μ, or greater than 1.0μ, and may typically be about 0.005μ, depending upon the size of the area that is to be etched, or decorated by deposition. The electron beam may have a lower energy or beam intensity to slow the etch rate to improve etch control and relative etch ratios, or may be defocused to etch a wider area. The electron beam may be scanned to cover the desired etch area or to etch a desired shape. The etch areas may be made as small as the electron beam can focus, plus the mean free path of the generated chemical radicals, and the etch area may have a diameter of less than 1.0μ. The electron beam may be part of a scanning electron microscope (SEM), and the SEM may be used to provide an image of the process as etching occurs.

The surface material removed by the chemical radicals during the decoration and contrast operations may be analyzed by well known analytical methods, including downstream analysis systems such as residual gas analyzer (RGA), mass spectroscopy, optical emission spectroscopy, atomic absorption spectroscopy, infrared spectroscopy, and Raman spectroscopy. The surface may be directly analyzed by various methods such as energy dispersive analysis of X-rays (EDAX), XES, or other SEM based analytic methods. This analysis may provide information on the materials present on the surface, and may be used to determine the appropriate etch environment to use in the contrast and decoration processes.

The optimum reactive material may be selected by choosing a chemical radical, or combination of radicals, that preferentially etches one material faster than other materials, such as fluorine radicals etch silicon oxides, and various types of glasses, at a much higher rate than fluorine radicals etch metals or organic materials. By using a radical material or mixture having a high etch ratio for oxides over nitrides, it is possible to substantially remove a glass layer underlying a nitride particle and to thus greatly increase the contrast between the two different dielectric materials, thereby increasing the sensitivity of the SEM image.

In an embodiment, the vacuum chamber and electron beam are a part of a scanning electron microscope (SEM), and the progress of etching and decorating deposition may be observed by the SEM. The etching and deposition operations may be terminated when the SEM image is optimized for the specific combination of materials present.

Another illustrative embodiment of the invention includes a system for localized chemical etching and deposition, including a vacuum chamber and a fixture for positioning a sample, a system, such as a gas inlet jet, for creating a layer of a chemical reactant proximate to the surface of the sample. An energetic beam, such as an electron beam from a SEM, is directed at the surface of the sample to form chemical radicals in the chemical reactant, such as xenon difluoride for an etching ambient, which may etch the sample in the region around the site of the energetic beam. The ambient may also include chromium containing compounds for decoration depositions on the sample. Material removed during an etching process may be analyzed to determine the composition of various portions of the surface of the sample. Areas smaller than one micron in diameter may be etched or deposited to increase the contrast between different materials, or to decorate the surface to improve and enhance defect images on the sample substrate.

An illustrative embodiment of the invention includes an apparatus for enhancing detection of surface defects, including a vacuum chamber with a fixture disposed for positioning a sample chemical radical induced etching and radical induced deposition. There is a material inlet in the vacuum chamber for creating a layer of a selected chemical combination in proximity with the surface of the sample, and an energetic beam, such as an electron beam, having a selected diameter and a selected energy level directed at a selected location on the surface of the sample. The energetic beam forms chemical radicals in the chemical layer near the surface. These radicals etch the surface materials, or deposit materials on the surface. The apparatus includes an etch end-point detector and an imager for detecting surface defects.

The described embodiments are directed towards the use of an electron beam to activate an adsorbed material forming a layer on an IC chip, and forming chemical radicals to etch the surface material of the IC, but the disclosure is not so limited, and may be applied to other structures and devices, such as printed circuit boards (PCBs), multi-chip modules (MCMs), liquid crystal display (LCD) devices, electronic displays, micro-electromechanical devices (MEMs), or other manufactured electronic or mechanical devices requiring failure analysis testing and material identification. Other means of forming local chemical radicals other than electron beams are included in this disclosure, to include focused microwave beams, laser and maser beams, X-ray and other energetic radiation sources. The material used to form the chemical radicals may be a gas, an evaporated liquid, a sublimed solid, or may be chemically formed by mixing precursor materials at the surface of the structure to be analyzed, or mixed remotely from the surface and either passively or actively transported to the region around the surface of the IC, or other structure. The reactive material may be either adsorbed onto the surface, precipitated onto the surface, or form a fluid layer in proximity to the surface, including a gaseous layer in the region around the IC surface. The generated chemical radicals may be used to selectively etch the surface as described in the described embodiments, or may react with other provided, or already present materials, to form dielectric, conductive or other materials to become a local deposition reaction. Such depositions may be used to refill the previously etched region to return the IC to working condition.

Although specific embodiments have been illustrated and described herein, it will be appreciated by those of ordinary skill in the art that any arrangement that is calculated to achieve the same purpose may be substituted for the specific embodiments disclosed, described and shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosure includes any other applications in which embodiments of the above structures and fabrication methods are used. The scope of the embodiments of the present invention should be determined with reference to the appended claims, along with the full scope of equivalents to which such claims are entitled.

What is claimed is:

1. A method comprising:
positioning a surface to be examined in a vacuum chamber;
creating a layer of a reactive material in proximity with the surface;
exciting a portion of the layer of reactive material in proximity to the surface to form chemical radicals, the exciting performed in the vacuum chamber with a gas ambient including material to decorate a particle on the surface for imaging;
removing a portion of the surface in proximity to the excited portion of the layer of reactive material; and
continuing the creating, exciting, and removing steps until at least one of a plurality of stop criteria occurs.

2. The method of claim 1, wherein further after a first predetermined time period of removing a portion of the surface, the surface is examined for defects.

3. The method of claim 1, wherein the stop criteria include at least one of an optical image of a defect, a scanning electron microscope image of a defect, a predetermined time has elapsed, a predetermined thickness of the surface in proximity to the excited portion of the layer of reactive material is removed, and at least one of a plurality of materials is detected in a downstream analysis detector.

4. The method of claim 1, wherein an energetic beam excites the portion of the layer of reactive material in proximity to the surface.

5. The method of claim 4, wherein the energetic beam includes one of an electron beam, an ion beam, a laser beam, a maser beam, a microwave beam, and an X-ray beam.

6. The method of claim 1, wherein the surface includes an integrated circuit.

7. The method of claim 1, wherein the method includes removing a portion of a first material layer, and the surface includes an exposed portion of a second material layer below the first material layer.

8. The method of claim 7, wherein the removing a portion of the first material layer includes etching the entire thickness of at least one dielectric layer.

9. The method of claim 8, wherein the removing a portion of the first material layer includes stopping the etching at a surface of a conductive material layer.

10. The method of claim 8, wherein the removing a portion of the first material layer includes stopping the etching at a surface of a second dielectric material layer having different properties from the first material layer.

11. The method of claim 3, wherein the method includes:
using a scanning electron microscope to provide the vacuum chamber and the electron beam; and
imaging the surface during an etching cycle to determine when a stopping criterion of a best image contrast of the defect is obtained in the scanning electron microscope.

12. The method of claim 1, wherein the reactive material comprises a halogen.

13. The method of claim 1, wherein the reactive material is a gas.

14. The method of claim 12, wherein the reactive material is xenon fluoride.

15. The method of claim 1, wherein an area containing the chemical radicals has a diameter of less than 1.0μ.

16. The method of claim 3, wherein the downstream analysis detector includes at least one of residual gas analysis, mass spectroscopy, optical emission spectroscopy, atomic absorption spectroscopy, infrared spectroscopy and Raman spectroscopy.

17. The method of claim 1, wherein a vacuum pressure of the vacuum chamber is determined by a desired mean free path of the chemical radicals generated by the exciting the layer of reactive material in proximity to the surface.

18. A method comprising:
positioning a surface to be examined in a vacuum chamber;
creating a layer of a reactive material in proximity with the surface;
exciting a portion of the layer of reactive material in proximity to the surface to form chemical radicals;
depositing a material layer upon a portion of the surface in proximity to the excited portion of the layer of reactive material, the material layer including material selected to decorate a particle on the surface for imaging; and
continuing the creating, exciting, and depositing steps until at least one of a plurality of stop criteria occurs.

19. The method of claim 18, wherein further after a first predetermined time period of depositing a material layer on a portion of the surface, the surface is examined for defects.

20. The method of claim 18, wherein the stop criteria include at least one of an optical image of a defect, a scanning electron microscope image of a defect, a predetermined time has elapsed, and a predetermined thickness of the deposited material layer is reached.

21. The method of claim 18, wherein an energetic beam excites the portion of the layer of reactive material in proximity to the surface.

22. The method of claim 21, wherein the energetic beam includes one of an electron beam, an ion beam, a laser beam, a microwave beam, and an X-ray beam.

23. The method of claim 18, wherein the surface includes an integrated circuit.

24. The method of claim 18, wherein the method includes removing a portion of a first material layer, and the surface includes an exposed portion of a second material layer below the first material layer.

25. The method of claim 21, wherein the method includes:

using a scanning electron microscope to provide the vacuum chamber and an electron beam; and imaging the surface during a depositing cycle to determine when a stopping criterion of a best image contrast of a defect is obtained in the scanning electron microscope.

26. The method of claim 18, wherein the reactive material comprises a metallo-halide compound.

27. The method of claim 26, wherein the reactive material is a gas.

28. The method of claim 26, wherein the reactive material comprises a halogen, a silicon containing material, an oxidizer, a metallo-organic, a metallo-halide, and a chemically inert material.

29. The method of claim 18, wherein an area containing the chemical radicals has a diameter of less than 1.0μ.

30. The method of claim 18, wherein a vacuum pressure of the vacuum chamber is determined by a desired mean free path of the chemical radicals generated by the exciting the layer of reactive material in proximity to the surface.

* * * * *

UNITED STATES PATENT AND TRADEMARK OFFICE

CERTIFICATE OF CORRECTION

PATENT NO. : 8,026,501 B2
APPLICATION NO. : 12/869538
DATED : September 27, 2011
INVENTOR(S) : Mark J. Williamson et al.

It is certified that error appears in the above-identified patent and that said Letters Patent is hereby corrected as shown below:

On the title page, item (54), in "Title", delete "DEPOSTING" and insert -- DEPOSITING --, therefor.

In column 1, line 1, delete "DEPOSTING" and insert -- DEPOSITING --, therefor.

Signed and Sealed this
Twentieth Day of December, 2011

David J. Kappos
*Director of the United States Patent and Trademark Office*